United States Patent [19]

Stoddard et al.

[11] Patent Number: 5,222,600
[45] Date of Patent: Jun. 29, 1993

[54] AUTOCLAVE POUCH

[76] Inventors: James T. Stoddard, 1700 Northwood Ave.; Charles D. Stoddard, 1845 Darby Dr., both of Florence, Ala. 35630

[21] Appl. No.: 920,904

[22] Filed: Jul. 28, 1992

[51] Int. Cl.$^5$ .............................................. B65D 81/18
[52] U.S. Cl. ................... 206/370; 206/369; 206/439; 206/484.1; 383/87
[58] Field of Search ................ 206/370, 369, 438–440, 206/484, 484.1; 383/84, 86, 87

[56] References Cited

U.S. PATENT DOCUMENTS

| | | | |
|---|---|---|---|
| 2,709,467 | 5/1955 | Hoeppner | 383/87 |
| 3,409,063 | 11/1968 | Pokras | 383/87 |
| 3,685,720 | 8/1972 | Brady | 206/439 |
| 3,768,725 | 10/1973 | Pilaro | 206/439 |
| 3,819,106 | 6/1974 | Schuster | 206/439 |
| 4,010,785 | 3/1977 | Patik | 383/87 |
| 4,057,144 | 11/1977 | Schuster | 206/439 |
| 4,367,816 | 1/1983 | Wilkes | 206/439 |
| 4,660,721 | 4/1987 | Mykleby | 206/484.1 |
| 4,874,090 | 10/1989 | Dyke | 206/484.1 |

Primary Examiner—Jimmy G. Foster
Attorney, Agent, or Firm—Phillips & Beumer

[57] ABSTRACT

A receptacle for containing medical instruments for sterilization is constructed having first and second broad sides connected along side and bottom edges. These sides are in turn constructed of an outer layer of flexible, durable fabric material, an intermediate layer of a plastic film material forming a barrier to microorganisms, and, in a preferred embodiment, an inner layer of the fabric material. A cuff extends from one of the edges adjacent the opening and is invertable over the opening to close the opening.

8 Claims, 4 Drawing Sheets

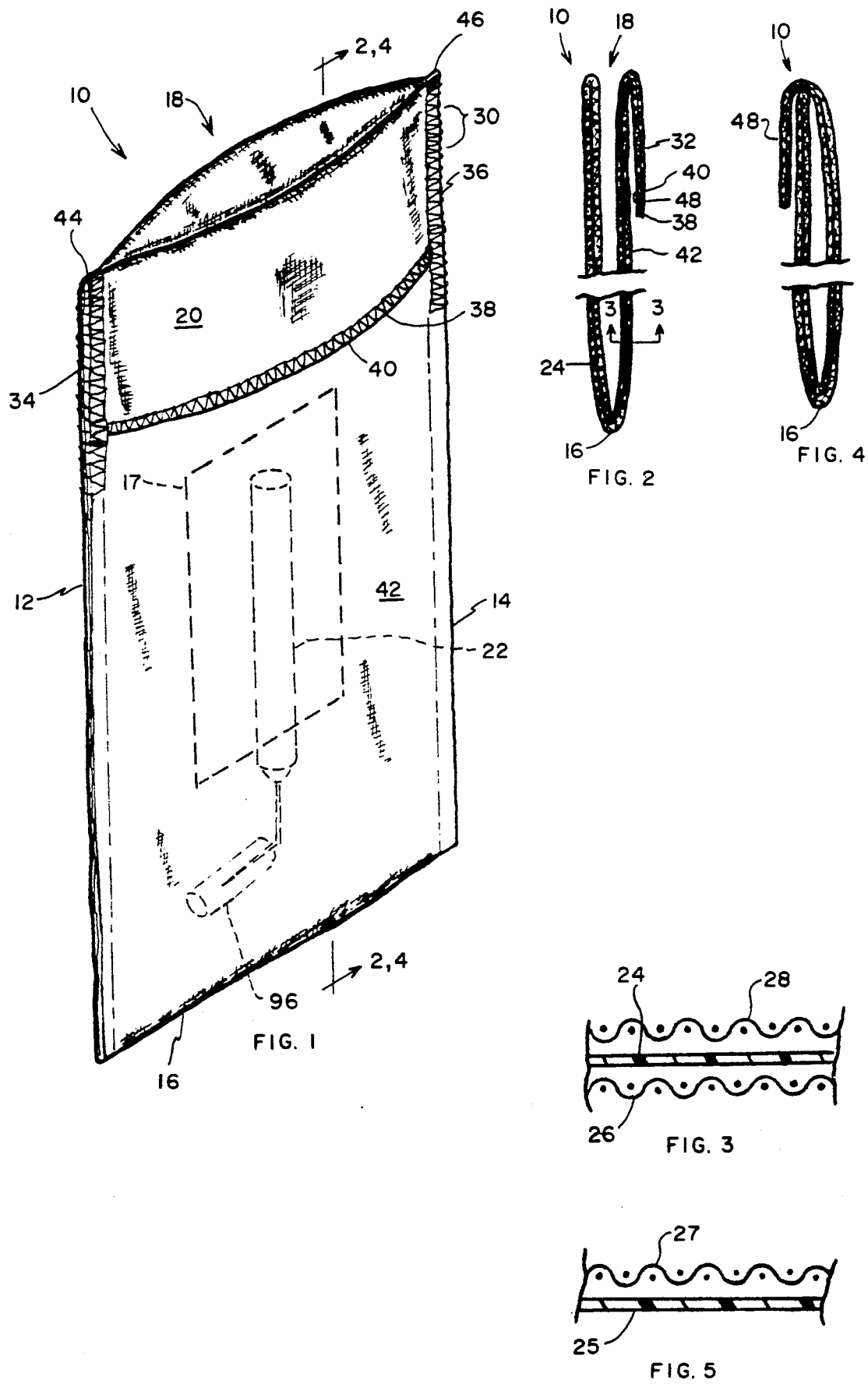

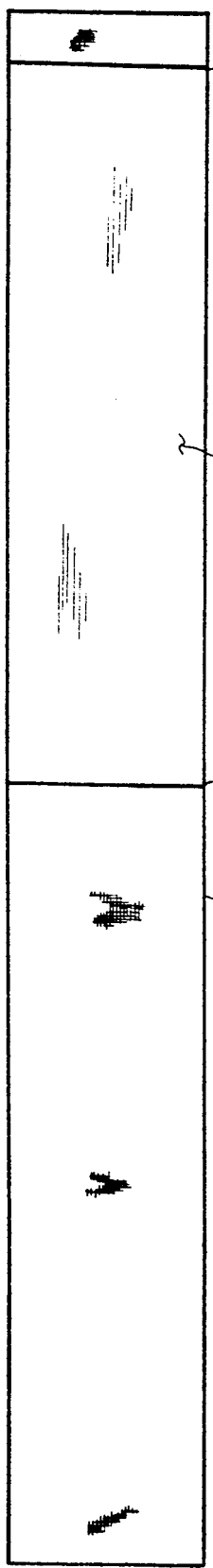
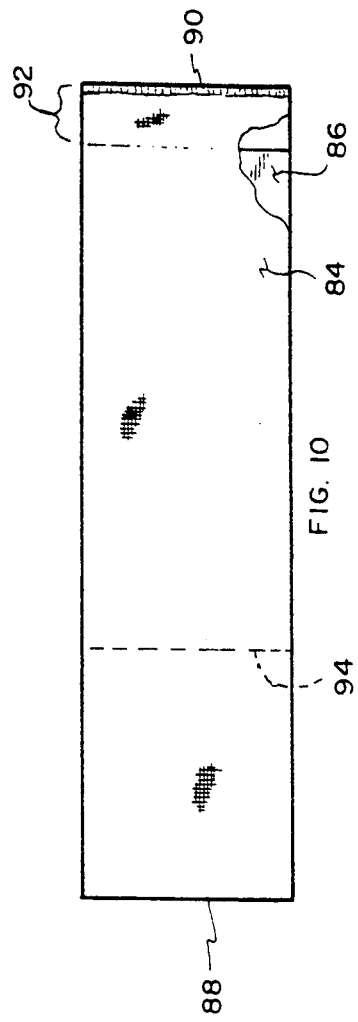
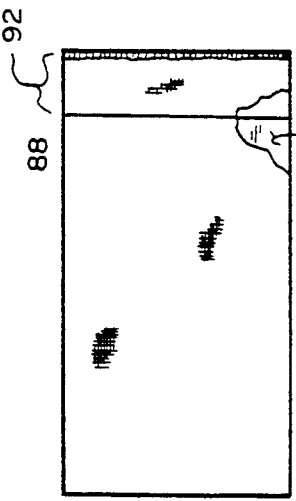
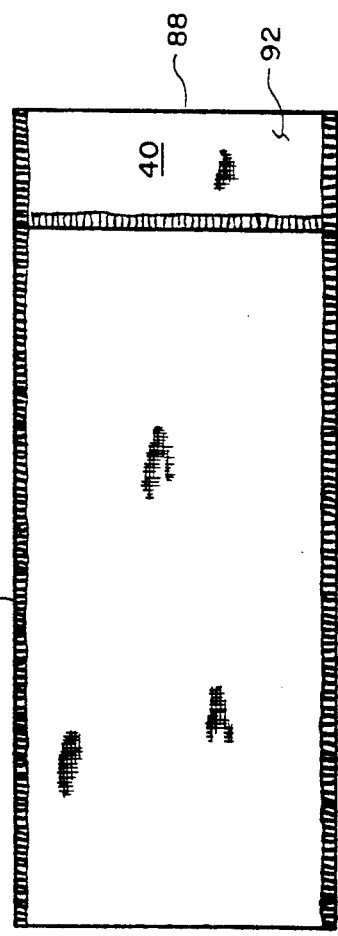

AUTOCLAVE POUCH

FIELD OF THE INVENTION

This invention relates generally to handling of articles possibly contaminated by viable biotoxic organisms and more particularly to a method for assisting in preventing accidental introduction of such organisms into an individual preparing surgical instruments for sterilization.

BACKGROUND OF THE INVENTION

With the emergence of AIDS, an insidious immunodeficient disease that occurs in humans caused most probably by an HIV retrovirus of simian origin, and commonly acquired by contact with blood and/or blood products from an infected individual, great concern has developed in the medical community over handling and sterilization of contaminated medical instruments. At present, as is commonly done, instruments used for invasive procedures by surgeons, dentists, nurses, and others of the medical profession are received or collected, typically by an individual who, during the last step of sterilizing the instruments in preparation for their next use, sorts the instruments in accordance with a particular protocol and sterilizes them in an autoclave which may utilize steam, dry heat, or a sterilizing toxic gas such as ethylene chloride. When the instruments are placed in the autoclave, they may be wrapped in a towel, placed in a disposable plastic bag and hermetically sealed, or, as is commonly done in hospitals, the instruments may be placed in paper bags or tubes constructed for the purpose of autoclaving instruments and simply taped shut.

In the instance where a number of instruments are assembled to form a kit for a particular application, such as a suture kit for repairing lacerations or cuts, the instruments may be packed together in a disposable plastic tray with a hermetically sealed plastic cover, with the tray containing the instruments being processed in an autoclave to effect sterilization of its contents. After the sterilization process is completed, the bags, trays, or other containers containing the instruments are removed from the autoclave, and, in the instance where they are to be used immediately, such as in a surgical or dental application, they are carried to the site of the procedure. If the instruments are stored for any length of time, they are placed in a relatively secure environment isolated from contaminating materials. When used, the containers are opened, the instruments removed, and the containers discarded.

One of the problems associated with these methods of preparation of instruments for sterilization is that the paper and plastic bags, even if the instruments are wrapped in gauze, are generally not durable enough to withstand the razor sharpness of scalpels and sharpened needle-like instruments, resulting in the bags being cut or punctured. Additionally, in the event the paper bags become wetted, as by condensation of steam in the autoclave, durability of the paper container is greatly decreased. Further, in a non-sterile environment, moisture can permeate the paper containers, carrying contaminants to the interior thereof and rendering instruments therein non-sterile. Further, the use of disposable bags greatly increases the quantity of medical waste and adds to medical costs inasmuch as the bags must be both procured and disposed of. Also, in the event where instruments are wrapped in towels to be sterilized, there is a possibility that they may be wrapped too tight or that too many instruments may be packed together, decreasing effectiveness of the sterilization process.

More importantly, while preparing the instruments for sterilization, the non-sterile instruments must be handled in order to place them in the aforementioned containers. Here, there is a distinct danger to the individual involved with the task of sterilizing the instruments of being accidentally pricked or cut by a contaminated sharpened instrument and possibly acquiring a communicable disease as a result.

Accordingly, it is an object of this invention to provide a method and apparatus that affords greater protection to individuals who handle surgical instruments in the process of sterilizing such instruments while eliminating the necessity of using disposable, non-durable paper and plastic bags during sterilization thereof.

SUMMARY OF THE INVENTION

A receptacle for holding medical instruments during and after sterilization is disclosed having first and second opposed sides constructed of a durable fabric material capable of withstanding temperatures of the autoclave. First, second, and third edges of the receptacle are connected, with fourth edges of the sides defining an opening to the pouch. A microorganism barrier material is disposed along interior sides of the first and second sides. An invertable cuff extends from one of the fourth edges and serves as a closure for the receptacle.

BRIEF DESCRIPTION OF THE DRAWINGS

FIG. 1 is a pictorial view of a receptacle of the present invention.

FIG. 2 is a broken sectional view taken along lines 2—2 of FIG. 1.

FIG. 3 is a sectional view of layered construction of the receptacle.

FIG. 4 is a sectional view taken along lines 4—4 of FIG. 1 illustrating a closure of the receptacle in a closed position.

FIG. 5 is a sectional view illustrating an alternate layered construction of the present invention.

FIGS. 9-12 are planar views illustrating a sequence of construction of a receptacle of the present invention.

DETAILED DESCRIPTION OF THE PREFERRED EMBODIMENT

Figure 6:
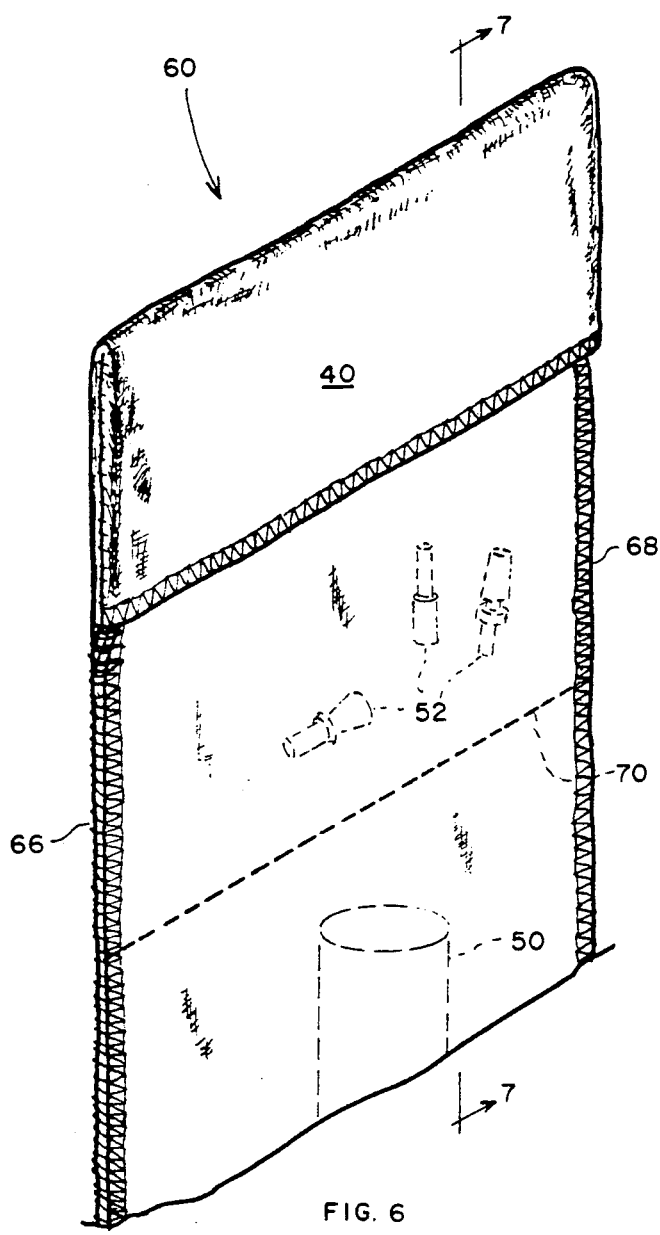
FIG. 6 is a partially cut-away view of an alternate embodiment of the invention.

Referring to FIG. 1, a reusable, autoclave receptacle 10 of a preferred embodiment of the present invention is shown. While receptacle 10, as described herein, is of particular construction, it is to be appreciated that construction or receptacle 10 may vary without departing from the intent of this invention. As shown, receptacle 10 is basically a flattened pouch or bag structure closed on sides 12, 14, and end 16, with open end 18 provided with a closure 20 for closing the receptacle. As such, medical instruments may be placed in receptacle 10, as illustrated by a dental pick 22 (dashed lines), for sterilization in an autoclave.

Receptacle 10, in a preferred embodiment as shown in FIGS. 1, 2, and 3, is constructed generally of a plastic, pliable film 24 of from about 1 to 5 mils thick, such as nylon, disposed between an inner layer 26 and an outer layer 28 of durable surgical or medical muslin or any other suitable surgical material, this material having a thread count of at least 160 or more threads per inch. The plastic film serves to provide a barrier against moisture and microorganisms that may penetrate the surgical muslin, while the inner and outer layers of surgical muslin greatly increase durability of the receptacle. Alternately, as shown in FIG. 5, a layered construction utilizing an inner layer 25 of plastic film and an exterior layer 27 of surgical muslin may be provided for facilitating cleaning of the receptacle by providing a smooth, flexible plastic interior to the receptacle.

Side edges 12 and 14 of receptacle 10 are constructed of open seams sewed closed, preferably by a serge-type stitch 30 (FIG. 1) having about 10 stitches per inch, for preventing the surgical muslin from ravelling. Closed end 16 is a seam formed by simply folding the material. If desired, a silicone sealer which forms an impervious film, as is available from a number or manufacturers, may be applied to the stitched regions for sealing such regions. In one embodiment, aligned openings 17 (dashed lines in FIG. 1) may be constructed in the inner and outer layers of muslin, and, with a transparent plastic film 24 used as the middle layer, a window in the receptacle is defined through which contents of the receptacle may be examined.

Closure 20 is constructed, in a preferred embodiment, and as shown in FIG. 2, as having a flap 32 of material formed as a folded extension of front inner and outer layers 26 and 28 of muslin, with sides 34 and 36 (FIG. 1) of flap 32 being sewn integral with sides 12 and 14, respectively, of the receptacle. During construction, end 38 of flap 32 is serged to prevent the muslin from ravelling and folded downward such that a cuff 40 is formed against front side 42 of the receptacle after being sewn as described along the edges. Cuff 40 is operated to close receptacle 10 by inverting upper corners 44 and 46 downward and through the interior of the cuff and inverting and folding the cuff over opening 18 such that inner side 48 of cuff 40 is exposed on an opposite side of receptacle 10, as shown in FIG. 4.

The seal effected by cuff 40, while being secure while being handled or carried to a site where a procedure is to be performed, is primarily designed for a situation where instruments are generally used on a frequent basis, such as in dentistry and the like. Where it is intended the receptacle and sterilized instruments therein is to be stored for a period of time, autoclave tape, which comprises a dye that changes color after undergoing the autoclave process, may be placed over the interface between cuff 40 and the receptacle prior to sterilization to indicate that contents of the receptacle have been sterilized. Further, the autoclave tape provides a convenient medium upon which a date the sterilization occurs may be placed.

Figure 7:
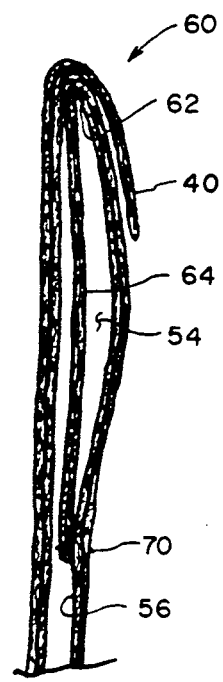
FIG. 7 is a sectional view partially cut away and taken along lines 7—7 of FIG. 6.

In the instance where several instruments or implements are used together during a procedure, such as a dental handpiece 50 (FIG. 6) having a chuck for coupling a number of differing drills, burrs, cleaning pads and other implements 52 to the handpiece, FIGS. 6 and 7 illustrate an embodiment of the present invention wherein a pocket 54 is constructed on an inner side 56 of a receptacle 60 constructed in the foregoing. An upper opening 62 to the pocket is formed on an inside region of receptacle 60 between a strip 64 of muslin and interior side 56 of the receptacle opposite from a side of the receptacle having cuff 40 thereon. Here, as with flap 30, strip 64 is sewn integral with receptacle 60 along sides 66 and 68 thereof and is sewed in a transverse direction along a bottom side to side 56, as illustrated by stitched line 70, defining the pocket 54 where small implements or instruments 52 may be placed for sterilization along with the handpiece. Pocket 54 may be constructed of any size as necessary and may extend partially along inner side 56, or extend the full length of side 54. Additionally, a plurality of pockets (not shown) may be constructed in a single receptacle such that each pocket may contain a plurality of identical burrs, drills, or the like, for sterilization. When cuff 40 is folded and inverted as described, opening 62 and the opening for receptacle 56 are covered by cuff 40, as shown in FIGS. 6 and 7.

Figure 8:
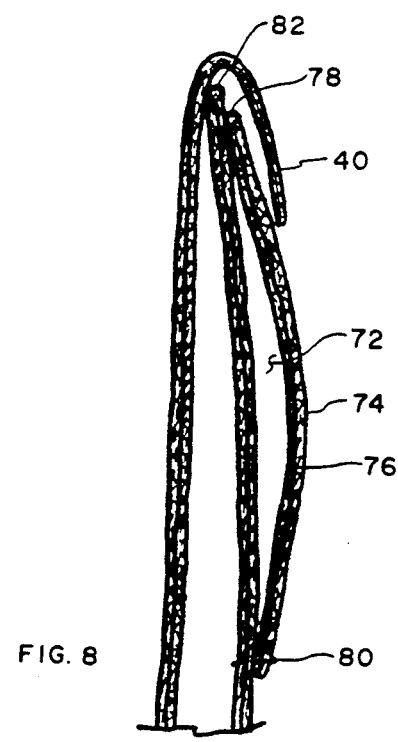
FIG. 8 is cut-away view of an alternate embodiment of the invention as shown in FIGS. 6 and 7.

For positioning the pocket on an exterior region of the receptacle so that certain medical instruments do not become entangled in the stitching of the opening of the receptacle or the stitching of the pocket, FIG. 8 illustrates an embodiment of the receptacle wherein an exterior pocket 72 is formed from a strip 74 of surgical muslin. Strip 74 is folded to enclose a plastic sheet 76, forming a fold 78, with ends of the strip 74 and plastic sheet 76 therebetween sewed to the receptacle at 80 and along sides to the receptacle as described above. Significantly, the folded region 78 is not aligned with the top of folded end 82 of the receptacle, but is downwardly offset about ¼", allowing easier access to pocket 72. Constructed as such, folded region 78 and folded end 82 of the receptacle define the opening in the receptacle and the opening of the pocket, precludimg a possibility of an instrument becomimg entangled in stitching. As shown in FIGS. 6, 7, and 8, cuff 40 is operated to close openings of the pocket and receptacle.

In order to categorize instruments in each receptacle, different colored thread for each different type receptacle may be used to indicate contents or use of contents of the receptacle. Additionally, such information may be printed or stamped on an exterior of the receptacle.

For constructing a receptacle of the present invention, and referring to FIG. 9, a surgical muslin strip 84 is cut having a width about ½" wider than a width of the finished receptacle and of a length generally four times that of the finished receptacle plus twice the length of cuff 40. A strip 86 or plastic film is cut having a like width as strips 84, but only about twice as long as the finished receptacle. Strip 86 is positioned as shown in FIG. 9 to cover strip 84 from a point 87 to a point 89 located at a midpoint of strip 84.

Strip 84 is then folded, as shown in FIG. 10, positioning plastic strip 86 between the folded sections of muslin strip 84. A folded end region 88 is formed in the muslin strip, with plastic strip 86 abutted against this folded end region 88. At an opposite end 90 of the folded muslin strip, the ends of muslin strips 84 are aligned and serged together, forming a cuff region 92 (dotted lines) at end 90 consisting of the ends of the muslin sections. Plastic strip 86 does not extend into cuff region 92 because it would render the cuff inordinately stiff. This folded strip is again folded in half as shown in FIG. 11 so that plastic strip 86 is folded in half and the partially completed receptacle turned over and cuff region 92 folded to cover an adjacent side as shown in FIG. 12 to form cuff 40. Sides 93 and 95 are then serged, closing sides of the receptacle and forming cuff 40. If desired, the aforementioned silicone sealer may then be applied to exterior stitches to fully seal the receptacle.

In the instance where an interior pocket is to be added, a strip of surgical muslin twice a length of the pocket and the same width as strips 84 and 86 is folded in half and the two ends serged together. The folded region of this strip is aligned with end 88 of the side of strip 84 shown in FIG. 10 and stitched at the serged end to the strip of FIG. 10 at about dotted line 94, forming an interior pocket as shown in FIG. 7. For forming an exterior pocket, a strip of muslin twice the length of the pocket is folded to enclose a plastic strip the length of the pocket, and the two ends and plastic strip are serged together. This serged strip is then positioned on an opposite side of strip 84 shown in FIG. 10, with the folded region thereof offset inward from about ¼" to ½' from end 88 and sewn to strip 84 at about dotted line 94. As such, an exterior pocket is formed as shown in FIG. 8, with the pocket and receptacle being closable by cuff 40 as shown in FIGS. 6, 7, and 8.

Figure 13:
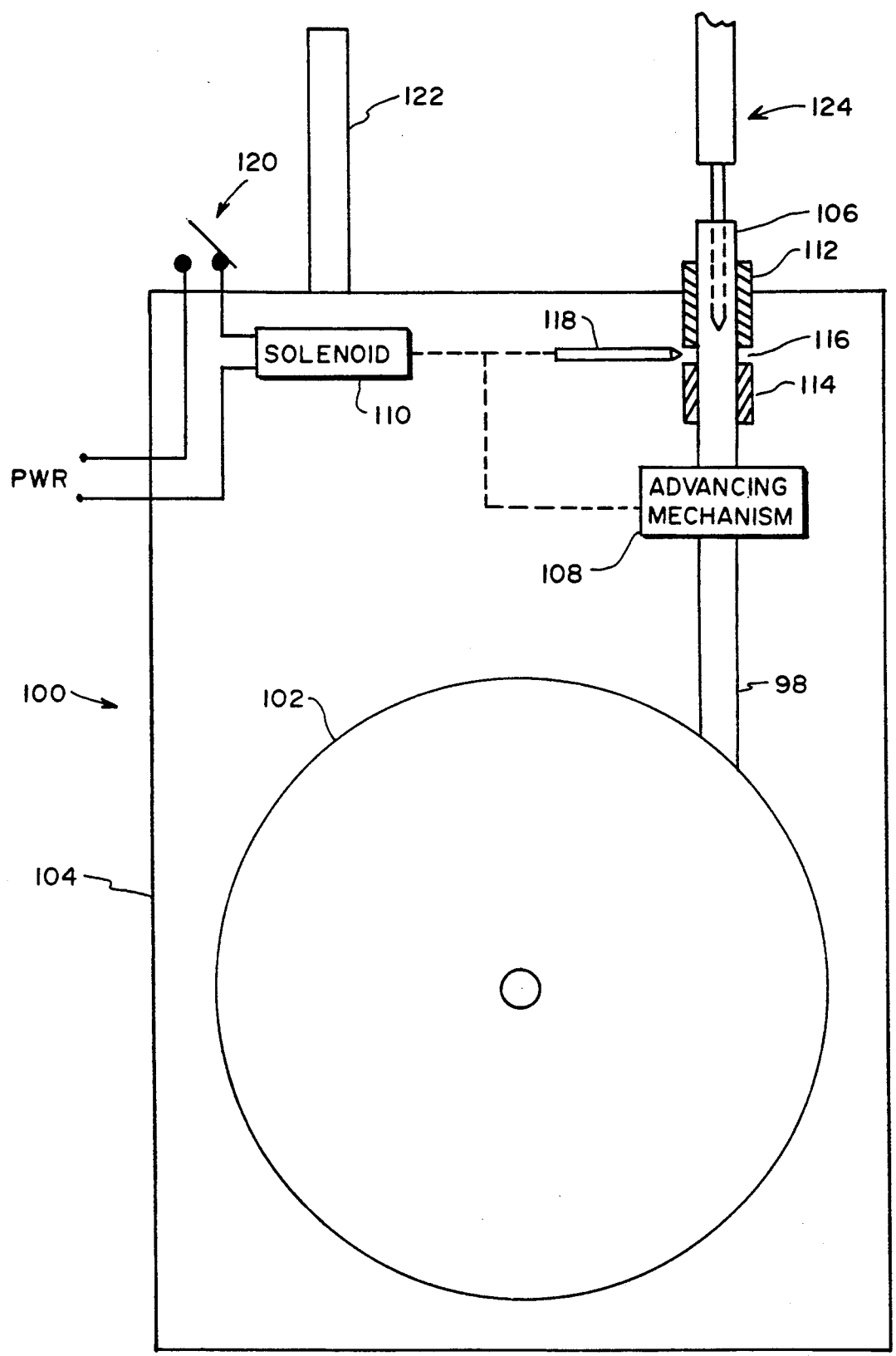
FIG. 13 is a diagrammatic view of a capping dispenser of the present invention.

FIGS. 1 and 13 illustrate a system wherein sharpened portions of needles and needle-like instruments, such as dental picks and the like, are capped by a cylindrical protective cap or sheath 96. Here, cap 96 is constructed from a flexible silicone closed cell sponge material 98 manufactured by AAA-Acme CME Rubber Corporation located in Tempe, Ariz. The intended use for this material is generally used as a gasket material in applications were temperature does not exceed about 450° F. and is constructed as a thickened cord or bead having a cross-sectional diameter of from about ⅛" to about ½" and supplied in rolls of about 40 feet. It has been found that lengths of from about ½" to 1" of this material may be used as protective caps to cap sharpened, potentially contaminated instruments prior to and during the sterilization process.

In addition to protecting individuals handling the instruments prior to and after sterilization, these caps additionally protect the receptacles by preventing sharp, needle-like instruments from puncturing the receptacles during handling. These lengths of material 98 are produced by a dispenser 100 as schematically illustrated in FIG. 13. Here, a roll 102 of the described capping material is housed in an enclosure 104, with an end 106 of the material extending through an advancing mechanism 108. Mechanism 108 may be a ratchet mechanism operated by solenoid 110, which serves to engage material 98 and upwardly advance a selected length thereof, such as the described ½" to 1" length. The material then extends through tubular support members 112 and 114, which provide support to material 98, with member 112 extending to the exterior of enclosure 104.

Members 112 and 114 are separated by a clearance 116 through which a knife 118 is forced by solenoid 110, cutting free an upper length of the material. A switch 120, such as a pushbutton type switch, is coupled to provide energizing electrical power to solenoid 120. A handguard 122 is positioned between switch 120 and end 106 of the material, for decreasing probability of an individual using dispenser 100 of incurring an accidental puncture wound from the contaminated instruments. After the instruments are capped, they are placed in an appropriate receptacle and sterilized in an autoclave as described.

In use, and as is typical of a sterilization procedure, contaminated instruments are placed in a neutral pH enzymatic detergent solution to generally clean the instruments. The instruments are then placed in a disinfectant solution in an ultrasonic cleaner for 10 to 30 minutes to disinfect and further clean the instruments. After being rinsed, the instruments are placed in a lubricating, anticorrosive solution commonly referred to as "surgical milk" for one minute. Next, the instruments are packaged for sterilization, with sharpened regions of dental picks or other needle-like instruments, as illustrated by instrument 124 of FIG. 13, being forced coaxially into end region 106 of material 98 and switch 120 operated to cut free a length of material 98. The instrument may then be safely placed in a receptacle as described above, the closure inverted to close the receptacle, which in turn is placed in an autoclave for sterilization.

Having thus described our invention and the manner of its use, it is apparent that incidental changes may be made thereto without departing from the scope of the following appended claims, wherein we claim:

1. A receptacle for containing medical instruments during and after a sterilization process comprising:
   a first, outer, side having first, second, third, and fourth edges, and of a length generally corresponding to lengths of said instruments to be sterilized, and constructed of a flexible fabric material able to withstand temperatures on the order of 250° F.;
   a second, outer, side having first, second, third, and fourth edges, and of a length generally corresponding to lengths of said instruments to be sterilized, and constructed of a fabric material able to withstand temperatures on the order of 250°, said first and second sides being in opposed relation, with said first, second, and third edges of said sides being connected in terms of their numerically referenced edges, defining an opening of said pouch along said fourth edges for insertion of said instruments to be sterilized into said receptacle;
   an invertable cuff extending from said fourth edge of said first side and formed of said fabric material for retaining flexability of said fabric material; and
   a layer of microorganism barrier material capable of withstanding the temperature on the order of 250° F. covering an interior region of said first and second sides.

2. A receptacle as set forth in claim 1 comprising a third layer of said flexible fabric material covering an interior region of said microorganism barrier material and forming an interior of said pouch.

3. A receptacle as set forth in claim 2 comprising an interior pocket constructed of said fabric material and attached to an interior side of one of said sides, for placing smaller said instruments therein.

4. A receptacle as set forth in claim 2 comprising an exterior pocket having an outer side constructed of said fabric material, an inner side constructed of said microorganism barrier material, said pocket affixed to an exterior region of said second side.

5. A medical sterilization assembly comprising:
   a pouch in turn comprising a first, outer, side having first, second, third, and fourth edges, and of a length generally corresponding to lengths of said instruments to be sterilized, and constructed of a flexible fabric material able to withstand temperatures on the order of 250° F.;
   a second, outer, side having first, second, third, and fourth edges, and of a length generally corresponding to lengths of said instruments to be sterilized, and constructed of a fabric material able to withstand temperatures on the order of 250°, said first and second sides being in opposed relation, with said first, second, and third edges of said sides being connected in terms of their numerically referenced edges, defining an opening of said pouch along said fourth edges for insertion of instruments to be sterilized into said receptacle;

an invertable cuff extending from said fourth edge of said first side and formed of said fabric material for retaining flexability of said fabric material;

a layer of microorganism barrier material capable of withstanding the temperature on the order of 250° F. covering an interior region of said first and second sides;

at least one medical instrument positioned in said pouch interior of said microorganism barrier material; and said invertable cuff being positioned around said fourth edges of said sides, thereby enclosing said pouch.

6. A sterilization assembly as set forth in claim 5 comprising a third layer of said flexible fabric material covering an interior region of said microorganism barrier material and forming an interior of said pouch.

7. A sterilization assembly as set forth in claim 6 comprising an interior pocket constructed of said fabric material and attached to an interior side of one of said sides, for receiving and containing smaller ones of said instruments.

8. A sterilization assembly as set forth in claim 6 comprising an exterior pocket having an outer side constructed of said fabric material, and an inner side constructed of said microorganism barrier material, for receiving and containing smaller ones of said instruments.

* * * * *